United States Patent [19]
Sugihara et al.

[11] Patent Number: 5,190,629
[45] Date of Patent: Mar. 2, 1993

[54] ELECTROPHORESIS MEDIUM MEMBRANE

[75] Inventors: Mitsuru Sugihara; Masashi Ogawa, both of Saitama, Japan

[73] Assignee: Fuji Photo Film Co., Ltd., Kanagawa, Japan

[21] Appl. No.: 604,358

[22] Filed: Oct. 26, 1990

Related U.S. Application Data

[63] Continuation of Ser. No. 219,938, Jul. 15, 1988, abandoned.

[30] Foreign Application Priority Data

Jul. 16, 1987 [JP] Japan .................. 62-177978

[51] Int. Cl.⁵ .................................................. C25B 7/00
[52] U.S. Cl. .............................. 204/182.8; 204/299 R
[58] Field of Search .................. 204/296, 299 R; 428/500

[56] References Cited

U.S. PATENT DOCUMENTS

| | | | |
|---|---|---|---|
| 4,576,693 | 3/1986 | Kreisher et al. | 204/299 R |
| 4,594,064 | 6/1986 | Anderson | 204/299 R |
| 4,722,777 | 2/1988 | Ogawa et al. | 204/182.7 |

FOREIGN PATENT DOCUMENTS

| | | |
|---|---|---|
| 0169397 | 6/1985 | European Pat. Off. |
| 0105053 | 6/1983 | Japan ................ 204/182.8 |

*Primary Examiner*—John Niebling
*Assistant Examiner*—Kathryn Gorgos
*Attorney, Agent, or Firm*—McAulay Fisher Nissen Goldberg & Kiel

[57] ABSTRACT

An electrophoresis medium membrane comprises a planar support, a planar cover sheet, and a layer of an electrophoresis gel medium provided between the planar support and the planar cover sheet. The electrophoresis gel medium contains an aqueous polyacrylamide gel, which is prepared by cross-linking polymerization of an acrylamide compound and a cross-linking agent in the presence of water and a compound having at least one carbamoyl group as a denaturing agent (or modifier). The layer of the electrophoresis gel medium has both a predetermined gradual change (gradient) in layer thickness and a predetermined gradual change (gradient) in concentrations of the acrylamide compound and the cross-linking agent.

12 Claims, 1 Drawing Sheet

ELECTROPHORESIS MEDIUM MEMBRANE

This is a continuation of application Ser. No. 219,938, filed Jul. 15, 1988 now abandoned.

BACKGROUND OF THE INVENTION

1. Field of the Invention

This invention relates to an electrophoresis medium membrane containing an aqueous polyacrylamide gel for use in determination of base sequences in nucleic acids such as a DNA and a RNA.

2. Description of the Prior Art

In the technique for determining base sequences in nucleic acids such as a DNA and a RNA according to the chemical degradation process, the dideoxy process or the like, slab electrophoresis using an electrophoresis medium membrane containing an aqueous polyacrylamide gel (hereinafter referred to as a polyacrylamide gel membrane or simply as a gel membrane) is indispensable. In recent years, electrophoresis analysis has come into wide use. Also, with the advances made in the dideoxy process, there has arisen a need for a polyacrylamide gel membrane capable of accurately separating up to a high molecular part of a fragment of a nucleic acid.

On the other hand, in the case where a fragment of a nucleic acid is electrophoretically separated based on a difference in its molecular weight for the base sequence determination of the nucleic acid and an ordinary polyacrylamide gel membrane having a constant thickness is used for this purpose, the band intervals of the separated fragment become wider for a low molecular part and narrower for a high molecular part. As a result, the separation of the high molecular part of the nucleic acid fragment is deteriorated. Accordingly, in order to achieve good separation performance uniformly over a wide molecular weight range from a low molecular part to a high molecular part, there has heretofore been used a polyacrylamide gel membrane (gradient gel membrane) having a gradient in the acrylamide concentration or a gradient in the buffer concentration along the direction of electrophoretic migration. For example, Japanese Unexamined Patent Publication No. 60(1985)-235819 (EP 0 159 694A, U.S. Pat. No. 4,704,198) discloses a process of and an apparatus for producing an electrophoresis medium membrane containing a polyacrylamide gel and having a gradient in the polyacrylamide concentration (gel concentration gradient or pore size gradient) by polymerizing and cross-linking a thin layer of an aqueous solution containing acrylamide and a cross-linking agent on a support surface by use of ionized radiation such as electron beams. The apparatus for carrying out the disclosed process and the method of controlling the electron beams or the like for forming the concentration gradient in the gel membrane are very complicated. In general, gradient gel membranes require much time for preparation and cannot always be prepared successfully because of low reproducibility of the concentration gradient. Thus the gradient gel membranes have the drawback that it is difficult to prepare many gel membranes having the gradient with good reproducibility.

On the other hand, in preparation of a gel membrane, the gel membrane is generally formed between two flat glass sheets, and it is difficult to impart a desired gradient in the membrane thickness to the gel membrane. For this reason, no gel membrane having the membrane thickness gradient has heretofore been used.

As mentioned above, it was technically difficult to provide the gel membrane at least with the gradient of the gel concentration or of the membrane thickness. Therefore, no attention has heretofore been given to the use of both the concentration gradient and the membrane thickness gradient. Also, it has generally been known that, in the case where the gel membrane is provided with the gradient of only one of the gel concentration or the membrane thickness, a complicated gradient curve is necessary in order to obtain good separation performance and for separation of the high molecular part of a nucleic acid. However, it was found that, with a gel membrane having both the concentration gradient and the membrane thickness gradient, large effects can be obtained by a combination of simple gradient curves (or gradient straight lines) of the concentration and the membrane thickness, respectively. Furthermore, the aqueous polyacrylamide gel exhibits a different extent of swelling, depending on a difference in the concentration. Therefore, with the gradient gel membrane having a complicated concentration gradient curve, the gel membrane is readily deformed at the time the gel membrane after being subjected to electrophoresis and carrying a separated nucleic acid fragment image is peeled from the support. However, it was found that, with a gel membrane having a simple concentration gradient curve (or a concentration gradient straight line), little deformation of the gel membrane arises at the time of peeling thereof after electrophoresis is carried out.

SUMMARY OF THE INVENTION

The primary object of the present invention is to provide an electrophoresis medium membrane containing an aqueous polyacrylamide gel for use in determination of base sequences in nucleic acids such as a DNA and a RNA, which has substantially uniformly, high separation effects over a wide molecular weight range from a low molecular part to a high molecular part of a fragment of a nucleic acid.

Another object of the present invention is to provide an electrophoresis medium membrane exhibiting no or little deformation caused by swelling as compared with a gel membrane having a concentration gradient alone.

The present invention provides an electrophoresis medium membrane comprising a planar support, a planar cover sheet, and a layer of an electrophoresis gel medium provided between said support and said cover sheet, said electrophoresis gel medium containing an aqueous polyacrylamide gel, which is prepared by cross-linking polymerization of an acrylamide compound and a cross-linking agent in the presence of water and a compound having at least one carbamoyl group as a denaturing agent (or modifier), wherein said layer of said electrophoresis gel medium has both a predetermined gradual change (gradient) in layer thickness and a predetermined gradual change (gradient) in concentrations of said acrylamide compound and said cross-linking agent.

Substantially uniform, high separation effects can be obtained over a wide molecular weight range from a low molecular part to a high molecular part of a fragment of a nucleic acid with the electrophoresis medium membrane in accordance with the present invention wherein the gel medium layer has both the predetermined gradual change in layer thickness (i.e. a layer thickness gradient or a membrane thickness gradient) and the predetermined gradual change in concentrations of the acrylamide compound and the cross-linking agent (i.e. a concentration gradient of the aqueous polyacrylamide gel). Also, the electrophoresis medium membrane in accordance with the present invention exhibits no or little deformation caused by swelling as compared with a gel membrane having a concentration gradient alone, and enables accurate determination of base sequences in nucleic acids such as a DNA and a RNA.

The acrylamide compound (monomer) for use in the preparation of the electrophoresis gel medium may be, for example, acrylamide or an acrylamide homologue such as N-methylacrylamide, N,N-dimethylacrylamide, N-(hydroxymethyl)acrylamide, or diacetone acrylamide. These compounds may be used alone, or two or more of these compounds may be used in combination. Among these compounds, acrylamide is preferable. A combination of acrylamide with one or more of the other acrylamide compounds is also preferable.

The cross-linking agent may be selected from bifunctional cross-linking agents disclosed in "Electrophoresis," 2(4), 213–219 (1981) and "Electrophoresis," 2(4), 220–228 (1981), and tri- or poly-functional cross-linking agents disclosed in Japanese Unexamined Patent Publication No. 61(1986)-2058. The bifunctional cross-linking agents include, for example, N,N'-methylenebisacrylamide (BIS), N,N'-propylenebisacrylamide (PBA), diacrylamide dimethyl ether (DAE), 1,2-diacrylamide ethylene glycol (DEG), ethyleneureabisacrylamide (EUB), ethylenediacrylate (EDA), N,N'-diallyltartardiamide (DATD), and N,N'-bisacrylylcystamine (BAC). The trifunctional cross-linking agents include, for example, 1,3,5-triacryloylhexahydro-s-triazine (TAHT), triallyl cyanurate (TAC), and triallyl isocyanurate (TAIC). Among these cross-linking agents, BIS and TAHT are preferable. Also, two or more cross-linking agents may be used in combination.

The cross-linking agent is used in a ratio within the range of approximately 1 wt % to approximately 30 wt % based on the total weight of the monomer and the cross-linking agent, preferably within the range of approximately 2 wt % to approximately 10 wt % based on the total weight of the monomer and the cross-linking agent.

The gel medium may also be added with agarose, which may be selected from low-electroendosmotic agarose, medium-electroendosmotic agarose, and high-electroendosmotic agarose as disclosed in, for example, Japanese Unexamined Patent Publication Nos. 55(1980)-5730, 55(1980)-110946, 57(1982)-502098 and 59(1984)-126236. The amount of agarose added may be within the range of approximately 0.2% w/v to approximately 2.0% w/v based on the volume of the aqueous gel containing the monomer and the cross-linking agent, preferably within the range of approximately 0.3% w/v to approximately 1.2% w/v based on the volume of the aqueous gel containing the monomer and the cross-linking agent.

The gel medium may also be added with a water-soluble polymer which may be a water-soluble, nonionic addition or condensation polymer having a molecular weight within the range of approximately 10,000 to approximately 1,000,000 as disclosed in, for example, Japanese Unexamined Patent Publication No. 59(1984)-126236 or 60(1985)-60548, a cross-linkable acrylamide copolymer containing a vinylsulfonyl group or the like as disclosed in, for example, Japanese Unexamined Patent Publication No. 61(1986)-18852, or a water-soluble cellulose derivative as disclosed in, for example, Japanese Patent Application No. 61(1986)-214878. The water-soluble, nonionic addition polymer may be, for example, polyacrylamide, polyvinyl alcohol, or polyvinyl pyrrolidone. The water-soluble nonionic condensation polymer may be, for example, polyethylene glycol, polypropylene glycol, or poly-N-vinyl pyrrolidone. The cross-linkable acrylamide copolymer may be, for example, a N-[[3-(vinylsulfonyl)propaneamide]methyl]acrylamideacrylamide copolymer, or a N-[[3-(2-chloroethylsulfonyl)-propaneamide]methyl]acrylamide-acrylamide-N-1,1-dimethyl-3-oxobutyl)acrylamide copolymer. The water-soluble cellulose derivative may be, for example, a water-soluble cellulose ether such as methyl cellulose, ethyl cellulose, hydroxyethyl cellulose, hydroxypropylmethyl cellulose or hydroxybutylmethyl cellulose. Among the above-enumerated water-soluble polymers, polyacrylamide, polyethylene glycol, and the N-[[3-(vinylsulfonyl)propaneamide]methyl]acrylamideacrylamide copolymer are preferable. In the case where the water-soluble, nonionic addition or condensation polymer is employed as the water-soluble polymer, the amount thereof added may be within the range of approximately 2 wt % to approximately 100 wt % based on the total weight of the monomer and the cross-linking agent, preferably within the range of approximately 5 wt % to approximately 50 wt % based on the total weight of the monomer and the cross-linking agent. In the case where the cross-linkable acrylamide copolymer is employed as the water-soluble polymer, the amount thereof added may be within the range of approximately 1 wt % to approximately 50 wt % based on the weight of the acrylamide compound, preferably within the range of approximately 5 wt % to approximately 40 wt % based on the weight of the acrylamide compound.

In order to prevent broadening of the band width in the electrophoretic image of the high molecular part of the nucleic acid fragment and distortion of the separation image, the gel medium may be added with glycerol in a ratio within the range of approximately 0.1% w/v to approximately 1.0% w/v based on the volume of the gel medium. Also, a polyol compound such as glycerol or ethylene glycol may be added as a wetting agent to the gel medium in a ratio within the range of approximately 1.0% w/v to approximately 40% w/v based on the volume of the gel medium.

The addition of agarose and/or the water-soluble polymer to the gel medium or the addition of the polyol compound such as glycerol or ethylene glycol should preferably be carried out at the time between dissolution of the monomer and the cross-linking agent into water and formation of the aqueous polyacrylamide gel.

The gel medium may be added with a nonionic, anionic or amphoteric surface active agent. The nonionic surface active agent may be, for example, the compound having the formula of

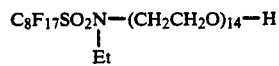

The anionic surface active agent may be, for example, the compound having the formula of

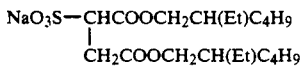

The amphoteric surface active agent may be, for example, the compound having the formula of

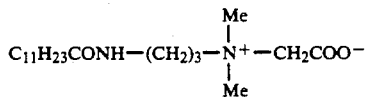

In the case where the nonionic or cationic surface active agent is used, the amount thereof added may be within the range of approximately $1 \times 10^{-4}\%$ w/v to approximately $5 \times 10^{-1}\%$ w/v based on the volume of the aqueous gel containing the monomer and the cross-linking agent, preferably within the range of approximately $1 \times 10^{-3}\%$ w/v to approximately $1 \times 10^{-2}\%$ w/v based on the volume of the aqueous gel containing the monomer and the cross-linking agent. In the case where the anionic surface active agent is used, the amount thereof added may be within the range of approximately $1 \times 10^{-4}\%$ w/v to approximately $5 \times 10^{-2}\%$ w/v based on the volume of the aqueous gel containing the monomer and the cross-linking agent, preferably within the range of approximately $1 \times 10^{-3}\%$ w/v to approximately $5 \times 10^{-2}\%$ w/v based on the volume of the aqueous gel containing the monomer and the cross-linking agent.

The compound having at least one carbamoyl group such as urea or formamide is used as the denaturing agent (or modifier). The amount of the denaturing agent added is within the range of approximately 40% w/v to approximately 60% w/v based on the volume of the aqueous gel containing the monomer and the cross-linking agent. In the case where urea is used as the denaturing agent, the amount thereof used may be within the range of approximately 6 mols (approximately 360 g) to the saturation amount (approximately 420 g) per 1,000 ml of the aqueous gel containing the monomer and the cross-linking agent, preferably within the range of approximately 7 mols to the saturation amount per 1,000 ml of the aqueous gel containing the monomer and the cross-linking agent. Since the amount of the denaturing agent added is comparatively large, the addition thereof should preferably be carried out at the time the ingredients containing the monomer and the cross-linking agent are dissolved into water.

A known pH buffer agent may be contained in the gel medium for adjusting the pH value during the electrophoresis to a value within the range of 8.0 to 9.0. The pH buffer agent may be selected from those described in "Kagaku Benran Kiso-hen" (Chemical Handbook, Fundamentals Ed.), Nihon Kagaku Kai, Maruzen, Tokyo, 1966, pp. 1312-1320; R.M.C. Dawson et al., "Data for Biochemical Research," 2nd ed., Oxford at the Clarendon Press, 1969, pp. 476-508; "Biochemistry," 5, pp. 467-477, 1966; and "Analytical Biochemistry," 104, pp. 300-310, 1980. By way of example, the pH buffer agent may be an agent containing tris(hydroxymethyl)aminomethane (Tris); N,N-bis(2-hydroxyethyl)glycine (Bicine); 4-(2-hydroxyethyl)-1-piperazinepropanesulfonic acid (HEPPS), Na salt or K salt; β-hydroxy-4-(2-hydroxyethyl)-1-piperazinepropanesulfonic acid (HEPPSO), Na salt or K salt; 3-[[2-hydroxy-1,1-bis(hydroxymethyl)ethyl]amino]-1-propanesulfonic acid (TAPS), Na salt or K salt; 3-(cyclohexylamino)-1-propanesulfonic acid (CAPS), Na salt or K salt; or an acid, an alkali or a salt may be combined, when necessary, with one of the above-enumerated compounds. An example of preferable buffer agents is Tris-boric acid-EDTA.2Na salt (composition for pH8.2-8.3).

In general, for the detection or reading of the electrophoretic image, the gel medium should preferably be substantially colorless and transparent in the form of a membrane having a predetermined thickness.

The gel medium is provided as a layer or a membrane having a predetermined, controlled gradual change in thickness on a substantially electrically non-conductive, water-impermeable, planar sheet-shaped (film-shaped or plate-shaped) support or cover sheet having a flat, smooth surface. A known glass plate, an organic polymer sheet, or the like may be used as the substantially electrically non-conductive, water-impermeable, planar support or cover sheet having a smooth surface. The organic polymer sheet may be formed of, for example, polyethylene terephthalate, bisphenol A polycarbonate, polystyrene, or a polymer of cellulose ester (for example, cellulose diacetate, cellulose triacetate or cellulose acetate propionate). The organic polymer sheet may be a planar sheet-shaped material or a plate-shaped material having a smooth surface and a thickness within the range of approximately 50 μm to approximately 2 mm, preferably within the range of approximately 80 μm to approximately 500 μm, and transparent, i.e. permeable to at least a part of electromagnetic radiations having a wavelength within the range of approximately 200 nm to approximately 900 nm. In the case where the organic polymer support or the cover sheet is used, in order to make the surface hydrophilic and to improve adhesion to the gel membrane, the organic polymer support or the cover sheet may be subjected to known surface processing such as irradiation of ultraviolet rays, glow discharge processing, corona discharge processing, flame treatment, irradiation of electron beams, chemical etching or electrolytic etching. On the surface of the organic polymer support or the cover sheet, a subbing layer or an adhesive layer as disclosed in, for example, Japanese Unexamined Patent Publication Nos. 59(1984)-164950, 59(1984)-212753, 60(1985)-194349, 60(1985)-239658, 60(1985)-244850 and 61(1986)-14557 may be provided when necessary to strengthen the adhesion of the support or the cover sheet to the gel medium layer. Also, as will be described later, a planar support or planar cover sheet having a predetermined gradual change in thickness may be used.

The gel medium is prepared by casting or applying an aqueous solution containing the aforesaid ingredients and a radical polymerization initiator composition (hereinafter often referred to as liquid for gel formation) in the layer or membrane form onto the support or the cover sheet, and polymerizing and cross-linking the monomer (acrylamide compound) with the cross-linking agent in the absence of molecular oxygen, when necessary with irradiation of ultraviolet rays or visible light or with heating, thereby forming a layer or a membrane of the aqueous polyacrylamide gel medium.

The acrylamide compound (monomer) and the cross-linking agent are dissolved or dispersed in water, and subjected to cross-linking polymerization in water to form the polymerized and cross-linked aqueous gel medium. In this specification, both dissolution (in water) and dispersion (in water) are generically referred to as dissolution (in water), and both the aqueous solution and the aqueous dispersion are generically referred to as the aqueous solution. Not only water but also a water-organic solvent mixture containing an organic solvent which may be added optionally may be used as the solvent or the dispersion medium.

The radical polymerization initiator composition may be selected from low-temperature radical polymerization initiator compositions described in "Electrophoresis," 2(4), 213–219 (1981), "Electrophoresis," 2(4), 220–228 (1981), Japanese Unexamined Patent Publication No. 59(1984)-126236, and "Saishin Denkieidoho" (Up-to-date Electrophoresis) by Aoki and Nagai (1973). The radical polymerization initiator composition may be, for example, a $\beta$-(dimethylamino)propionitrile (DMDPN) - ammonium peroxodisulfate mixture, a N,N,N',N'-tetramethylethylenediamine (TEMED) - ammonium peroxodisulfate mixture, a TEMED - riboflavin mixture, a TEMED - riboflavin - hydrogen peroxide mixture, a riboflavin - ammonium peroxodisulfate mixture, or a riboflavin - hydrogen peroxide mixture. (In the case where the photosensitizer such as riboflavin is used in combination, irradiation of ultraviolet rays or visible light is used in combination.) The amount of the radical polymerization initiator composition added is within the range of approximately 0.3 wt % to approximately 5.0 wt % based on the total weight of the monomer and the cross-linking agent, preferably within the range of approximately 0.5 wt % to approximately 3.0 wt % based on the total weight of the monomer and the cross-linking agent.

The gel concentration is adjusted such that the total weight of the monomer and the cross-linking agent is within the range of approximately 3% w/v to approximately 30% w/v based on the volume of the gel medium consisting of the monomer, the cross-linking agent and water, as expressed in accordance with the definition described in S. Hjerten, "Archives of Biochemistry and Biophysics," 1(Suppl.), 147–151 (1962).

In the course of the cross-linking polymerization of the liquid for gel formation on the surface of the support (or the cover sheet), the casting or application of the liquid for gel formation and the cross-linking polymerization should preferably be carried out in the absence of molecular oxygen, for example, in a nitrogen gas atmosphere, or the cross-linking polymerization should preferably be carried out by covering the surface of the case or applied liquid for gel formation by a covering material such as a cover film, a cover sheet or a cover plate exactly after the casting or application of the liquid for gel formation. The covering material used for this purpose may be formed of the same material as the aforesaid support. In the case where an organic polymer film is used as the cover film, the thickness thereof may be approximately 300 $\mu$m or less, practically within the range of approximately 4 $\mu$m to approximately 200 $\mu$m, preferably within the range of approximately 4 $\mu$m to approximately 100 $\mu$m. In the case where a glass plate is used as the covering material, the thickness thereof may be nearly equal to the thickness of the planar glass plate used as the support.

In general, the concentration gradient of the acrylamide compound and the cross-linking agent in the gel medium membrane (i.e. the concentration gradient of the aqueous polyacrylamide gel) is provided such that the concentration is lower on the pouring inlet side for a nucleic acid sample and is higher on the sample outlet side. Also, the thickness gradient of the gel medium membrane is generally provided such that the thickness is smaller on the pouring inlet side for the nucleic acid sample and is larger on the sample outlet side. However, different gradients may also be employed in accordance with the purposes. The gel membrane thickness gradient and the concentration gradient (curves or straight lines) as the features of the gel medium membrane in accordance with the present invention may be represented by a part of a gradual change line expressed by a function of a straight line, a slightly bent straight line, an exponential function, a logarithmic function, a catenary, a pursuit curve, a parabola, a hyperbola, an ellipse, or a curve of third degree, by any other gradual change line, or by a combination of a curve with a straight line, with respect to the distance from the edge of sample spotting portion. The extent of the change in thickness may be within the range of approximately 50 $\mu$m to approximately 5 mm, preferably within the range of approximately 80 $\mu$m to approximately 1,000 $\mu$m. The range of the concentration gradient of the acrylamide compound and the cross-linking agent (i.e. the concentration gradient of the aqueous polyacrylamide gel) is from approximately 3 wt % to approximately 30 wt %, preferably from approximately 4 wt % to approximately 25 wt %. Any combination of the aforesaid gradient forms may be employed as the combination of the membrane thickness gradient with the concentration gradient. However, the membrane thickness gradient and the concentration gradient should preferably be combined such that the membrane thickness is gradually increased monotonously and the concentration is gradually decreased monotonously as the distance from the edge of sample spotting portion increases along the direction of electrophoretic migration, or such that the membrane thickness is maintained substantially constant up to a middle point in the direction of electrophoretic migration and is increased from the middle point whereas the concentration is decreased up to a middle point and is maintained substantially constant from the middle point. Alternatively, the membrane thickness gradient and the concentration gradient should preferably be combined such that the membrane thickness is gradually decreased monotonously and the concentration is gradually increased monotonously as the distance from the sample pouring edge increases along the direction of electrophoretic migration, or such that the membrane thickness is decreased up to a middle point in the direction of electrophoretic migration and is maintained substantially constant from the middle point whereas the concentration is maintained substantially constant up to a middle point and is increased from the middle point. Also, the shape of the sample pouring portion may be selected from known shapes such as a rectangle, a square, a triangle (shark's teeth shape), and a circle.

The method of providing the gel medium membrane with the membrane thickness gradient may be selected from (i) a method wherein a spacer plate having a thickness change nearly corresponding to the predetermined, controlled gradual change in thickness (layer thickness gradient or membrane thickness gradient) is secured to the support, and the liquid for gel formation is poured into a mold formed by covering with a covering material (sheet-shaped material) along the spacer plate and subjected to cross-linking polymerization, (ii) a method wherein a spacer plate having constant thickness is secured to the surface of the support (or the cover sheet) having a thickness change corresponding to the predetermined gradual change in thickness, and the liquid for gel formation is poured into a mold formed by covering with a covering material (support) along the spacer plate and subjected to cross-linking polymerization, (iii) a method wherein the liquid for gel formation is cast onto the surface of the support (or the cover sheet) having a thickness change corresponding to the predetermined gradual change in thickness, and is subjected to cross-linking polymerization in the absence of molecular oxygen, for example, in a nitrogen gas atmosphere, and (iv) a method wherein the liquid for gel formation is cast or applied onto the surface of the support (or the cover sheet) by controlling the flow rate per unit time so as to correspond to the predetermined gradual change in thickness (so that the flow rate is lower for the region of smaller gel membrane thickness and is higher for the region of larger gel membrane thickness), and is subjected to cross-linking polymerization in the absence of molecular oxygen, for example, in a nitrogen gas atmosphere. The support having the predetermined gradual change in thickness may be prepared by a known process such as the mold casting process, the chemical etching process, and the cutting process. In the case where the liquid for gel formation is cast or applied onto the surface of the support (or the cover sheet) by controlling the flow rate, the thickness change of the spacer plate need not necessarily correspond to the predetermined gradual change in the thickness of the gel membrane. Also, instead of providing the membrane thickness gradient of the gel medium over the overall width of the gel membrane, the membrane thickness gradient may be provided only over regions having widths slightly broader than the regions of the electrophoresis lanes in accordance with the number of the lanes, and the remaining regions may have substantially constant thicknesses. This configuration can be achieved advantageously in the case where the support or the cover sheet having a gradual change in thickness is used.

In order to provide the gel medium membrane with the gel concentration gradient, it is possible to employ an apparatus described in "Tanpakushitsu.Koso No Kisojikkenho" (Basic Experimental Method for Proteins and Enzymes), Horio and Yamashita, Nankodo, 1981, pp. 304–308, and Japanese Unexamined Patent Publication No. 54(1979)-43881, wherein a vessel containing an aqueous solution which contains a monomer (acrylamide), a cross-linking agent and a polymerization initiator composition in relatively high concentrations and a vessel containing an aqueous solution which contains the monomer (acrylamide), the cross-linking agent and the polymerization initiator composition in relatively low concentrations are connected with each other by a conduit (the vessel containing the high-concentration aqueous solution is disposed at a position higher than or at the same height as the vessel containing the low-concentration aqueous solution), and the vessel containing the low-concentration aqueous solution is connected by a conduit with a casting or applying apparatus via a pump. With this apparatus, the aqueous solution is delivered from the vessel containing the low-concentration aqueous solution while the aqueous solution is stirred and, at the same time, the high-concentration aqueous solution moves by its weight into the vessel containing the low-concentration aqueous solution, so that the liquid levels of both aqueous solutions are maintained equal. In this manner, the concentration of the low-concentration aqueous solution is increased gradually. Therefore, the concentration gradient of acrylamide and the cross-linking agent is given rise to in the casting or applying apparatus, and a desired gel concentration gradient is obtained after the cross-linking polymerization.

The gel medium membrane in accordance with the present invention can be prepared in the same manner as the known aqueous polyacrylamide gel medium membrane. Also, the gel medium membrane in accordance with the present invention can be used for horizontal and vertical slab electrophoresis in accordance with the known processes described in the above-mentioned references.

DESCRIPTION OF THE PREFERRED EMBODIMENTS

The present invention will hereinbelow be described in further detail with reference to the following examples and the accompanying drawings.

EXAMPLE 1 AND COMPARATIVE EXAMPLE 1

A 10 mm-wide, 40 cm-long spacer plate having a constant thickness of 300 $\mu$m was secured by adhesion to both edges at longer sides of a rectangular, colorless, transparent polyethylene terephthalate (PET) film as a planar support having a size of 20 cm×40 cm and a thickness of 180 $\mu$m and having a smooth surface made hydrophilic by irradiation of ultraviolet rays. A liquid for gel formation having the composition indicated in column A in Table 1 below and a liquid for gel formation having the composition indicated in column B in Table 1 were respectively cast onto the supports obtained in the manner as mentioned above by use of the concentration gradient forming apparatus as mentioned above. In each case, the casting was carried out in a nitrogen gas atmosphere by stirring the liquid for gel formation and changing the thickness of the membrane of the liquid for gel formation on the support by controlling the flow rate in such a range that the thickness of the membrane of the liquid for gel formation was from 150 $\mu$m to 300 $\mu$m. Each of the membranes of the liquids for gel formation was subjected to cross-linking polymerization by irradiation from a 500W xenon luminescent lamp in a nitrogen gas atmosphere. Then, a rectangular, colorless, transparent PET sheet having a thickness of 63 $\mu$m and a size of 20 cm×40 cm as a cover sheet was overlaid in close contact with each of the thus formed gel membranes. In this manner, aqueous polyacrylamide gel membranes (1) and (2) having a change in the thickness of the gel cross-section and a change in gel concentration as shown in FIGS. 1 and 2 were prepared.

On the other hand, a gel membrane (3) having a constant thickness of 200 μm and a gel concentration gradient (Comparative Example 1-1) was prepared in the same manner as Example 1, except that the flow rate of the liquid for gel formation was maintained constant so that the membrane of the liquid for gel formation had a thickness of 200 μm. Also, a gel membrane (4) having a constant thickness of 200 μm and a constant gel concentration (Comparative Example 1-2) was prepared in the same manner as Example 1, except that a liquid for gel formation having a composition indicated in column C in Table 1 was used and the flow rate of the liquid for gel formation was maintained constant so that the membrane of the liquid for gel formation had a thickness of 200 μm.

Figure 1:
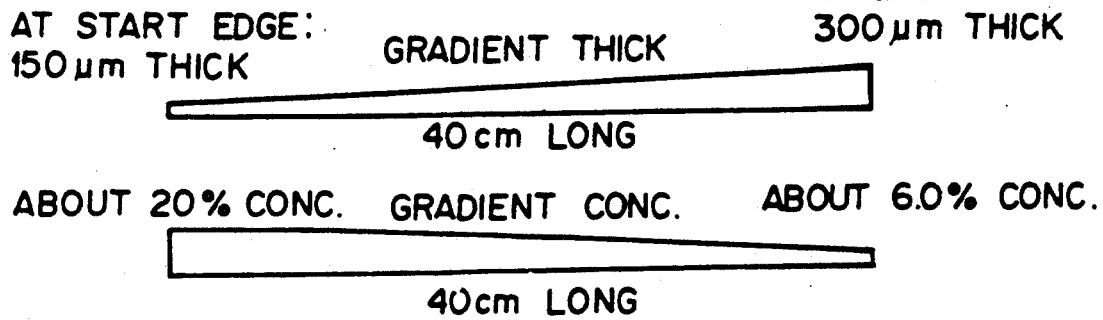
FIGS. 1 and 2 are explanatory sectional views showing a gradual change in thickness (membrane thickness gradients) and a gradual change in gel concentration (concentration gradients) of gel membranes (1) and (2) in Example 1 in accordance with the present invention along the direction of electrophoretic migration.
Figure 2:
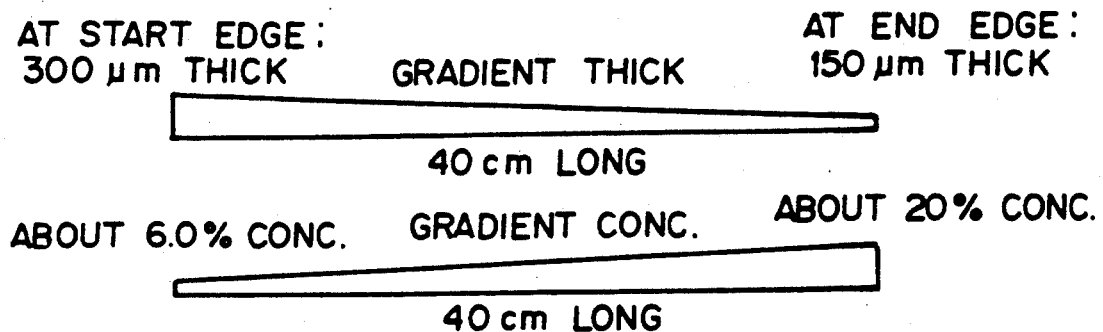

Gel membrane (1) (FIG. 1)

The thickness was linearly increased from the minimum of 150 μm at the start edge in the direction of electrophoretic migration to the maximum of 300 μm at the end edge in the direction of electrophoretic migration. The gel concentration was decreased nearly in the form of a part of a circular arc from the maximum of approximately 20% at the start edge in the direction of electrophoretic migration to the minimum of approximately 6.0% at the end edge in the direction of electrophoretic migration.

Gel membrane (2) (FIG. 2)

The thickness was linearly decreased from the maximum of 300 μm at the start edge in the direction of electrophoretic migration to the minimum of 150 μm at the end edge in the direction of electrophoretic migration. The gel concentration was increased almost linearly from the minimum of approximately 6.0% at the start edge in the direction of electrophoretic migration to the maximum of approximately 20% at the end edge in the direction of electrophoretic migration.

Figure 3:
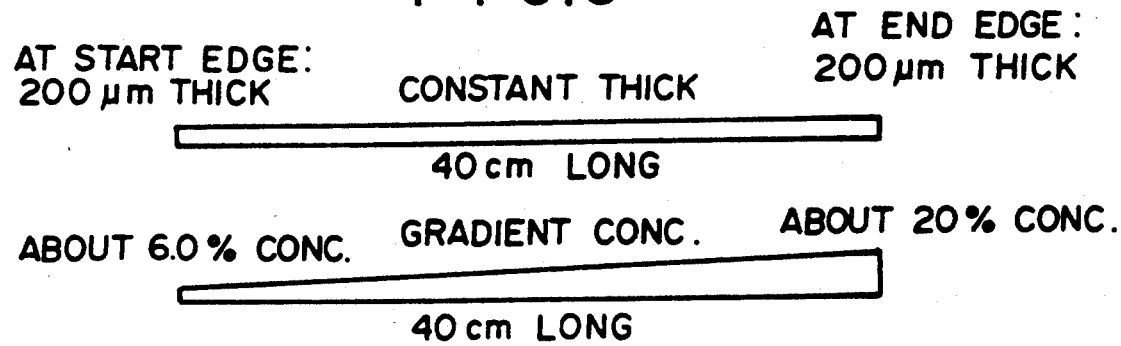
FIG. 3 is an explanatory sectional view showing the constant thickness and a gradual change in gel concentration (concentration gradient) of a gel membrane (3) in Comparative Example 1-1 along the direction of electrophoretic migration.

Gel membrane (3) (FIG. 3)

The thickness was constant at 200 μm. The gel concentration was increased almost linearly from the minimum of approximately 6.0% at the start edge in the direction of electrophoretic migration to the maximum of approximately 20% at the end edge in the direction of electrophoretic migration.

Figure 4:
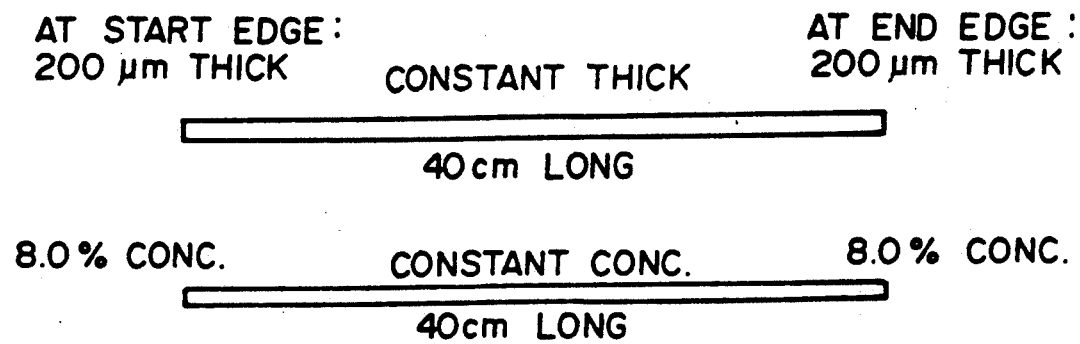
FIG. 4 is an explanatory sectional view showing the constant thickness and the constant gel concentration of a gel membrane (4) in Comparative Example 1-2 along the direction of electrophoretic migration.

Gel membrane (4) (FIG. 4)

The thickness was constant at 200 μm. The gel concentration was constant at approximately 8.0%.

Experiments for the base sequence determination of a DNA were carried out in accordance with the conventional method by using the four gel membranes obtained in the manner as mentioned above and DNA fragment samples prepared by the dideoxy process for M13-mp8DNA. As a result, it was found that the range of the readable base fragments with the gel membranes (1) and (2) having the combination of the membrane thickness gradient with the concentration gradient in accordance with the present invention was as shown below.

Gel membrane (1): No. 60 to No. 250
Gel membrane (2): No. 60 to No. 240

Also, the widths and intervals of the electrophoretic images of the base fragments in the respective lanes were within the readable range and were not narrowed extremely.

On the other hand, with the gel membrane (3) having the constant thickness and the gel concentration gradient and the gel membrane (4) having the constant thickness and the constant gel concentration in accordance with the conventional technique, the readable range was as shown below.

Gel membrane (3): No. 60 to No. 220
Gel membrane (4): No. 60 to No. 200

With the gel membrane (4), the widths and intervals of the electrophoretic images of the base fragments in the respective lanes were narrowed gradually from the low molecular part to the high molecular part.

Thus, the experiments revealed that, with the electrophoresis medium membrane containing the aqueous polyacrylamide gel and having both the membrane thickness gradient and the concentration gradient in accordance with the present invention, the electrophoretic image intervals are maintained almost uniformly over a wide molecular weight range from the low molecular part to the high molecular part of a base fragment of a nucleic acid, and good separation is obtained. Also, with the electrophoresis medium membrane in accordance with the present invention, the number of readable base fragments is large, and the base sequence determination of a nucleic acid such as a DNA can be carried out accurately.

TABLE 1

| | Composition of Liquid for Gel Formation | | |
|---|---|---|---|
| Ingredient | A | B | C |
| Acrylamide | 19.15 g | 5.745 g | 7.66 g |
| 1,3,5-Triacryloyl-hexahydro-s-triazine | 850 mg | 255 mg | 340 mg |
| Agarose | 450 mg | — | — |
| Urea | 42.0 g | — | — |
| [pH buffer agent] | | | |
| Tris | 1.21 g | — | — |
| Boric acid | 650 mg | — | — |
| EDTA.2Na | 75 mg | — | — |
| Made up to 100 ml with water | | | |
| [Polymerization initiator] | | | |
| Ammonium peroxodisulfate (5 wt % aqueous solution) | 1.3 ml | — | — |
| N,N,N',N'-tetramethyl-ethylenediamine (25 wt % aqueous solution) | 33 μl | — | — |
| Na riboflavin phosphate ester (0.25 wt % aqueous solution) | 1.5 ml | — | — |

Agarose: Low electroendosmotic, gelling temperature 36° C.
—: Indicates the same value and the same unit as in the left column.

We claim:

1. An electrophoresis medium membrane for use in separating fragments of nucleic acid comprising a planar support, a planar cover sheet, and a layer of an electrophoresis gel medium provided between said support and said cover sheet, said electrophoresis gel medium containing an aqueous polyacrylamide gel, which is prepared by crosslinking polymerization of an acrylamide compound and a crosslinking agent in water and a compound having at least one carbamoyl group as a denaturing agent, wherein said layer of said electrophoresis gel medium has both a predetermined gradual change in layer thickness within the range from 50 μm to 5 mm and a predetermined gradual change in concentrations of said acrylamide compound and said cross-linking agent in the range from 3 to 30 weight percent.

2. An electrophoresis medium membrane as defined in claim 1 wherein said support and said cover sheet are planar sheet-shaped materials formed of an organic polymer.

3. An electrophoresis medium membrane as defined in claim 2 wherein said support and said cover sheet are planar sheet-shaped materials formed of polyethylene terephthalate.

4. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 3.

5. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 2.

6. An electrophoresis medium membrane as defined in claim 1 wherein said compound having at least one carbamoyl group is urea.

7. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 6.

8. An electrophoresis medium membrane as defined in claim 1 wherein said gel medium further contains agarose.

9. An electrophoresis medium membrane as defined in claim 8 wherein said gel medium further contains a water-soluble polymer.

10. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 4.

11. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 8.

12. In a method for the separation of DNA fragments from a mixture thereof wherein portions of the mixture are introduced to a gel medium membrane in an electrophoresis apparatus and subjected to an electric potential, the improvement which comprises the membrane being the membrane of claim 1.

* * * * *